United States Patent
Kimura et al.

(10) Patent No.: US 10,119,156 B2
(45) Date of Patent: Nov. 6, 2018

(54) GLUCOSE PRODUCTION METHOD AND GLUCOSE PRODUCED BY SAID METHOD

(71) Applicants: ACTEIIVE CORPORATION, Noda-shi, Chiba (JP); Masahiko Abe, Noda-shi, Chiba (JP); Kengo Sakaguchi, Tsukuba-shi, Ibaraki (JP); Shigeru Kido, Ishikawa-gun, Fukushima (JP)

(72) Inventors: Yoshihiro Kimura, Tokyo (JP); Misato Imai, Hokuto (JP); Hisayuki Kojima, Nara (JP); Yoshihiro Kanai, Takasaki (JP); Yasutaka Seki, Koshigaya (JP); Kenichi Aburai, Kasukabe (JP); Yukiko Kikuchi, Sapporo (JP)

(73) Assignees: ACTEIIVE CORPORATION, Noda-Shi (JP); Masahiko Abe, Noda-Shi (JP); Kengo Sakaguchui, Tsukuba-Shi (JP); Shigeru Kido, Ishikawa-Gun (JP)

( * ) Notice: Subject to any disclaimer, the term of this patent is extended or adjusted under 35 U.S.C. 154(b) by 0 days.

(21) Appl. No.: 14/891,952

(22) PCT Filed: May 19, 2014

(86) PCT No.: PCT/JP2014/063173
§ 371 (c)(1),
(2) Date: Nov. 17, 2015

(87) PCT Pub. No.: WO2014/185546
PCT Pub. Date: Nov. 20, 2014

(65) Prior Publication Data
US 2016/0090613 A1    Mar. 31, 2016

(30) Foreign Application Priority Data

May 17, 2013   (JP) ................. 2013-105209
Jul. 17, 2013   (JP) ................. 2013-148545
Nov. 12, 2013  (JP) ................. 2013-234006
May 9, 2014    (JP) ................. 2014-097515

(51) Int. Cl.
*C07H 3/02* (2006.01)
*C12P 19/02* (2006.01)
*C12P 19/14* (2006.01)
*C13K 1/02* (2006.01)
*C07H 1/08* (2006.01)

(52) U.S. Cl.
CPC ............. *C12P 19/02* (2013.01); *C07H 1/08* (2013.01); *C07H 3/02* (2013.01); *C12P 19/14* (2013.01); *C13K 1/02* (2013.01)

(58) Field of Classification Search
CPC . C12P 19/02; C12P 19/14; C07H 3/02; C07H 1/08; C13K 1/02
See application file for complete search history.

(56) References Cited

U.S. PATENT DOCUMENTS

| 8,785,154 B2 | 7/2014 | Boy et al. |
| 2011/0165277 A1* | 7/2011 | Ali et al. ................. 424/769 |
| 2012/0329100 A1 | 12/2012 | Uraki et al. |

FOREIGN PATENT DOCUMENTS

| JP | 2011519550 A | 7/2011 |
| JP | 2012085544 A | 5/2012 |
| WO | 2011111664 A1 | 9/2011 |
| WO | 2012147044 A1 | 11/2012 |

OTHER PUBLICATIONS

Katz M. et al., "Production of Glucose by Enzymatic Hydrolysis of Cellulose", Applied Microbiology, Feb. 1968, vol. 16, No. 2, pp. 419-420.*
Zhao J., "Turning Waste Into Food: Cellulose Digestion", Dartmouth Undergraduate Journal of Science, Fall 2010/Feb. 2011; accessed on Oct. 13, 2017 at the web at (http://dujs.dartmouth.edu/2011/02/turning-waste-into-food-cellulose-digestion/), pp. 1-5. (Year: 2010).*
Ke et al., "Advanced biorefinery in lower termite-effect of combined pretreatment during the chewing process", Biotechnology for Biofuels, 2012, 5:11 (http://www.biotechnologyforbiofuels.com/content/5/1/11), total pp. 1-14. (Year: 2012).*
Seki Y. et al. "Enhancement of cellulose degradation by cattle saliva", PLOS-one, Sep. 24, 2015, 10(9):e0138902. doi: 10.1371/journal.pone.0138902, total pp. 1-19. (Year: 2015).*
Borjesson, J. et al., Enhanced enzymatic A conversion of softwood lignocellulose by poly (ethylene glycol) addition, Enzyme Microb. Technol., Mar. 5, 2007, vol. 40, No. 5, pp. 754-762.
International Search Report (ISR) dated Jul. 15, 2014, issued for International application No. PCT/JP2014/063173.
Extended European Search Report (EESR) dated May 2, 2016, issued for corresponding European patent application No. EP14797675.
Slaytor et al., Cellulose digestion in termites and cockroaches: What role do symbionts play?, Comparative Biochemistry and Physiology, Dec. 1, 1992, p. 775-784, vol. 103, No. 4.
Veivers et al., Digestive enzymes of the salivary glands and gut of Mastotermes darwiniensis, Insect Biochemistry, Jan. 1, 1982, p. 35-40, vol. 12, No. 1.

* cited by examiner

*Primary Examiner* — Satyendra K Singh
(74) *Attorney, Agent, or Firm* — Law Office of Katsuhiro Arai (57) ABSTRACT

A glucose production method is characterized in that a cellulose raw material is decomposed using a mixture of a cellulolytic enzyme, and saliva or an activating auxiliary agent derived from biological saliva. The method achieves excellent glucose yield.

1 Claim, 6 Drawing Sheets

GLUCOSE PRODUCTION METHOD AND GLUCOSE PRODUCED BY SAID METHOD

This application is the U.S. National Phase under 35 U.S.C. § 371 of International Application PCT/JP2014/063173, filed May 19, 2014, which claims priority to Japanese Patent Application No. 2013-105209, filed May 17, 2013; No. 2013-148545, filed Jul. 17, 2013; No. 2013-234006, filed Nov. 12, 2013; and No. 2014-097515, filed May 9, 2014. The International Application was published under PCT Article 21(2) in a language other than English.

TECHNICAL FIELD

The present invention relates to a glucose production method that enables improvement in glucose yield from a cellulose raw material and glucose produced by this method.

BACKGROUND ART

In recent years, there has been an increase in the use of glucose in industrial applications as a starting material for bioethanol and polymeric materials that serve as alternative fuels for petroleum fuel.

Conventionally, as described in Patent Literature 1, glucose for industrial use has been produced from potatoes, grains such as corn, wheat, barley, rye, triticale, and rice, or plants used as raw material for sugar such as sugarcane and sugar beets. However, there is concern that, as industrial application accelerates, the transaction prices of grains and plants used as raw material for sugar that are traded for use as food will rise, thereby cutting into household budgets and playing a part in famine in developing countries.

Therefore, it is desirable that glucose be produced from cellulose raw materials that are non-food products, such as wood, grass, and rice straw, of which vast reserves can be found on Earth. Patent Literature 2 discloses the production of glucose from such cellulose raw materials.

Patent Literature 1: Japanese Patent Laid-open Publication No. 2011-915550
Patent Literature 2: Japanese Patent Laid-open Publication No. 2012-085544

DISCLOSURE OF INVENTION

Problem to be Solved by the Invention

However, cellulose raw materials have very rigid crystalline components. Therefore, to obtain glucose through enzymolysis without forcible saccharification n treatment being performed using a strong acid, as described in Patent Literature 2, a step of pelletizing the cellulose raw material, a step of immersing the cellulose raw material in an alkaline solution, or the like is generally performed as a pretreatment. However, even when such pretreatments are performed, it is difficult to significantly improve glucose yield.

Therefore, an object of the present invention is to provide a glucose production method that achieves excellent glucose yield, and glucose produced by this method.

Means for Solving Problem

Ruminant animals, such as cattle, donkeys, camels, sheep, and goats, obtain energy by saccharifying cellulose raw materials, such as straw, inside the body. The inventors of the present invention and the like have focused on the cellulose-decomposing function of ruminant animals that feed on cellulose raw materials. The inventors and the like have found that the saliva of these ruminant animals is an assisting factor in enzymolysis, and have thereby completed the present invention.

To achieve the above-described object, a first aspect of the glucose production method of the present invention is characterized in that cellulose is decomposed using a mixture of a cellulolytic enzyme, and saliva or an activating auxiliary agent derived from biological saliva. In addition, a second aspect of the glucose production method of the present invention is characterized in that the saliva is saliva from a ruminant animal, and the activating auxiliary agent is extracted from saliva from a ruminant animal. A third aspect of the glucose production method of the present invention is characterized in that the saliva from a ruminant animal is saliva from cattle, donkeys, camels, sheep, or goats.

According to the first to third aspects of the glucose production method of the present invention, glucose yield from a cellulose raw material can be significantly improved.

The glucose of the present invention is characterized by being produced using a glucose production method according to any of the first to third aspects.

Because the glucose of the present invention is produced at a high yield from a cellulose raw material, the glucose can be provided on the market at a low price.

Effect of the Invention

In the glucose production method of the present invention, glucose yield from a cellulose raw material can be significantly improved.

Furthermore, because the cellulose raw material is saccharified through relatively gentle enzymolysis, the cost of safety management in production plants can be reduced. As a result, glucose can be provided at a low price.

In addition, the glucose of the present invention can be produced at a high yield from a cellulose raw material. Therefore, glucose can be provided on the market at a low price.

EXPLANATIONS OF LETTERS OR NUMERALS

S1 pulverizing step
S2 enzymolysis step
S3 glucose purifying step
C cellulose raw material

BEST MODE(S) FOR CARRYING OUT THE INVENTION

A specific embodiment of a glucose production method of the present invention will hereinafter be described in detail with reference to FIG. 1 to FIG. 4.

The glucose production method of the present invention is a method for obtaining glucose by decomposing a cellulose raw material, such as wood, grass, or rice straw, using a mixture of a cellulolytic enzyme, and saliva or an activating auxiliary agent derived from biological saliva.

A cellulase containing three types of enzymes, endoglucanase, cellobiohydrolase, and β-glucosidase, can be used as the cellulolytic enzyme. Endoglucanase randomly cleaves cellulose at amorphous regions and thereby reduces the degree of polymerization of cellulose. Cellobiohydrolase decomposes cellulose in cellobiose units, from crystalline region terminals. β-glucosidase decomposes cellobiose into glucose.

The type of cellulase is not particularly limited, and may be a commercially available cellulase, or a cellulase derived from bacteria, plants, or the like. However, glucose yield can be further improved through use of a cellulase derived from Trichoderma, which is excellent for cellulose decomposition.

As the saliva or the activating auxiliary agent derived from biological saliva, saliva from a ruminant animal or an activating auxiliary agent extracted from the saliva can be used. The ruminant animal includes, for example, cattle, donkeys, camels, sheep, and goats. In particular, when the glucose production method of the present invention is industrially implemented, a predetermined amount of saliva can be stably supplied when saliva from cattle is used.

In addition, as the activating auxiliary agent derived from biological saliva, an organic compound contained in the biological saliva can be used.

According to the specific embodiment of the glucose production method of the present invention such as that described above, as shown in FIG. 1, the following steps are performed: a pulverizing step S1 of pulverizing a cellulose raw material C into a predetermined particle size; an enzymolysis step S2 of performing enzymolysis on the pulverized cellulose Cf that has been pulverized, using a mixture of a cellulolytic enzyme, and saliva or an activating auxiliary agent derived from biological saliva; and a glucose purifying step S3 of purifying the glucose produced at the enzymolysis step S2.

Figure 1:
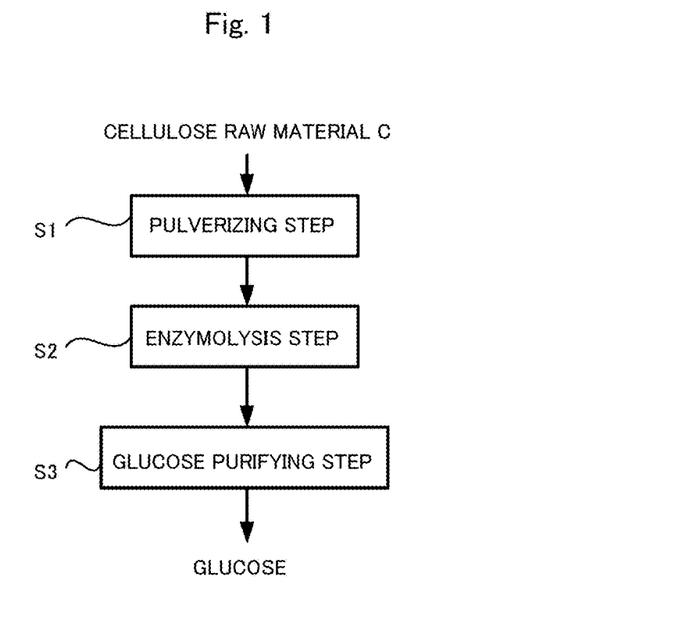
FIG. 1 is a flowchart of production steps in a glucose production method according to an embodiment of the present invention.

At the pulverizing step S1, in particular, the obtained pulverized cellulose raw material Cf preferably has a small particle size. As a result of amorphous regions of the cellulose being exposed, enzymolysis by the cellulolytic enzyme can be facilitated, and the glucose yield can be further improved.

The pulverizing step S1 can be omitted in cases where the particle size of the cellulose raw material C is sufficiently small.

Furthermore, in addition to the above-described steps, for example, a liquefying step of dissolving the cellulose raw material C in an ionic liquid, a basic solvent such as ethylenediamine, or the like to impart fluidity to the cellulose can be used.

In the glucose production method of the present invention such as that described above, the method is for producing glucose from the cellulose raw material C by enzymolysis. At the enzymolysis step S2, enzymolysis is performed through use of the mixture of a cellulolytic enzyme, and saliva or an activating auxiliary agent derived from biological saliva. As a result, decomposition of the cellulose raw material C by the cellulolytic enzyme can be promoted, and the glucose yield from the cellulose raw material C can be significantly improved.

Furthermore, because the cellulose raw material is saccharified through relatively gentle enzymolysis, the cost of safety management in production plants can be reduced. As a result, the produced glucose can be provided at a low price.

Specific examples of the glucose production method of the present invention will be described below.

EXAMPLE 1

In example 1, glucose was produced using saliva from cattle as the saliva from living matter.

In the present example, Avicel (manufactured by Merck & Co., Inc.), which is a microcrystalline cellulose, was used as the cellulose raw material. Avicel at a concentration of 1% was added to a 50 mM buffer solution, and a 10 μg/mL substrate suspension was obtained. A cellulase (Trichoderma Viride (manufactured by Sigma-Aldrich Corporation)) was used as the cellulolytic enzyme. 500 μg of the cellulase per 1 mL of the 50 mM buffer solution was diluted five-fold with the reaction mixture, and finally a 100 μg/mL enzyme was used in the reaction mixture. Undiluted saliva collected from the mouths of cattle that has been diluted 50-fold with the reaction mixture was used as the saliva from cattle. As the buffer solution, an aqueous sodium acetate solution having a pH of 4.0 was used in each instance.

In the glucose production method of the present example, first, 15 μL of the 100 μg/mL enzyme solution and 15 μL of the cattle saliva were added to 120 μL of the 10 μg/mL substrate suspension serving as the cellulose raw material C. Incubation was performed for 24 hours at 50° C. (this sample is referred to, hereafter, as sample A).

To examine the production amount of glucose by the glucose production method of the present invention, incubation for 24 hours at 50° C. was also performed on each of: sample B obtained by adding only 15 μL of the 100 μg/mL enzyme solution to 120 μL of the 10 μg/mL substrate suspension, and adjusting the resultant to a total amount of 150 μL with the buffer solution; sample C obtained by adding only 15 μL of the cattle saliva to 120 μL of the 10 μg/mL substrate suspension, and adjusting the resultant to a total amount of 150 μL with the buffer solution; and sample D obtained by adjusting only 120 μL of the 10 μg/mL substrate suspension to a total amount of 150 μL with the buffer solution.

Figure 2:
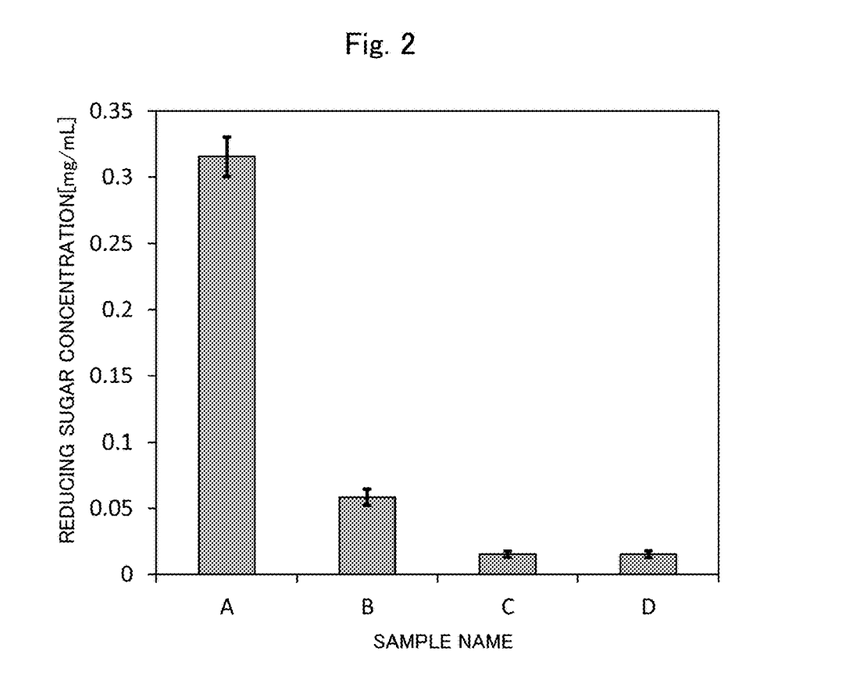
FIG. 2 is a graph of the glucose yield from each sample in example 1 of the glucose production method of the present invention.

The results of calculation of reducing sugar concentrations using the Somogyi-Nelson method after incubation are indicated in FIG. 2.

In the present example, as shown in FIG. 2, 0.32 mg/mL of reducing sugar was detected from sample A for which the glucose production method of the present invention was used; 0.06 mg/mL of reducing sugar was detected from sample B in which only the cellulase had been added to the cellulose raw material C; 0.02 mg/mL of reducing sugar was detected from sample C in which only the cattle saliva had been added to the cellulose raw material C; and 0.02 mg/mL of reducing sugar was detected from sample D containing only the cellulose raw material C. The values indicated in FIG. 2 are the mean values of three samples, and the standard deviations thereof are indicated as error bars.

Based on the results, about five-times the amount of reducing sugar was detected from sample A, compared to that of sample B in which only the cellulase had been added to the cellulose raw material C. It is clear that enzymatic activity of the cellulase significantly improves as a result of cattle saliva being added. In addition, because an equivalent amount of reducing sugar was not detected from either sample C in which only cattle saliva had been added to the cellulose raw material C or sample D containing only the cellulose raw material, it is clear that the cellulose raw material C cannot be decomposed into glucose by the cattle saliva alone.

Example 1, described above, indicates that, through use of the glucose production method of the present invention, glucose yield from a glucose raw material can be improved by about five-fold. As a result, provision of glucose to the market at a low price can be actualized.

EXAMPLE 2

In example 2, glucose was produced using an activating auxiliary solution obtained by an organic compound being extracted from cattle saliva, as the activating auxiliary agent derived from biological saliva.

Here, the method for extracting an organic compound from cattle saliva will be described.

First, 10 ml of cattle saliva is boiled for 10 minutes. The protein component within the saliva that has been denatured by heat is adsorbed into a solid-phase extraction column (Oasis HLB 12 cc (500 mg) LP Extraction Cartridge, manufactured by Waters Corporation). A 100% aqueous methanol solution is added to the solid-phase extraction column, and a solution containing organic compounds is extracted. In addition, evaporation, drying, and solidification are performed by a nitrogen stream, and a solid matter is obtained. The obtained solid matter is dissolved in a buffer solution to 1 mg/mL. An auxiliary agent solution is thereby prepared. Through use of an aqueous methanol solution as an elution solvent, the methanol concentration in 200 µL of the auxiliary agent solution is increased over time from 0% to 100%, and purification is performed by high-performance liquid chromatography. Fractionation is performed every 5 minutes for a period of 40 minutes, and a total of eight types of activating auxiliary agent solutions containing organic compounds of differing polarities are obtained.

Glucose was produced using the total of eight types of activating auxiliary agent solutions obtained through purification from the cattle saliva, instead of the cattle saliva, by the glucose production method of the present invention, described in detail in example 1. In the present example, sample 1 is an activating auxiliary agent solution separated when the methanol concentration is about 5%; sample 2 is an activating auxiliary agent solution separated when the methanol concentration is about 21%; sample 3 is an activating auxiliary agent solution separated when the methanol concentration is about 37%; sample 4 is an activating auxiliary agent solution separated when the methanol concentration is about 53%; sample 5 is an activating auxiliary agent solution separated when the methanol concentration is about 68%; sample 6 is an activating auxiliary solution separated when the methanol concentration is about 84%; sample 7 is an activating auxiliary solution separated when the methanol concentration is about 100%; and sample 8 is an activating auxiliary solution separated when the methanol concentration is 100% (0% water). In addition, the glucose raw material and the cellulolytic enzyme described in example 1 were used.

Figure 3:
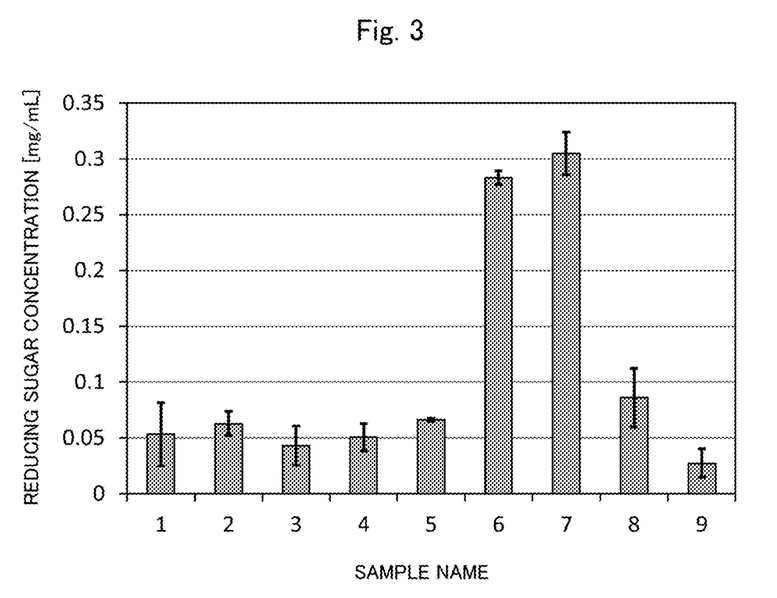
FIG. 3 is a graph of the glucose yield from each sample in example 3 of the glucose production method of the present invention.

The results of glucose production using sample 1 to sample 8, and as a comparison, the result of glucose production from sample 9, prepared by the process for sample B in example 1, are shown in FIG. 3.

In the present example, as shown in FIG. 3, 0.05 mg/mL of reducing sugar was detected from sample 1 having a methanol concentration of about 5%; 0.06 mg/mL of reducing sugar was detected from sample 2 having a methanol concentration of about 21%; 0.04 mg/mL of reducing sugar was detected from sample 3 having a methanol concentration of about 37%; 0.05 mg/mL of reducing sugar was detected from sample 4 having a methanol concentration of about 53%; 0.07 mg/mL of reducing sugar was detected from sample 5 having a methanol concentration of about 68%; 0.28 mg/mL of reducing sugar was detected from sample 6 having a methanol concentration of about 84%; 0.31 mg/mL of reducing sugar was detected from sample 7 having a methanol concentration of about 100%; 0.09 mg/mL of reducing sugar was detected from sample 8 having a methanol concentration of 100% (0% water); and 0.03 mg/mL of reducing sugar was detected from sample 9 in which only the cellulase was added to the cellulose raw material. The values indicated in FIG. 3 are the mean values of three samples, and the standard deviations thereof are indicated as error bars.

In particular, sample 6 having a methanol concentration of about 84% and sample 7 having a methanol concentration of about 100% showed very high reducing sugar concentrations. Based on these results, it is clear that enzymatic activity is promoted by the activating auxiliary agent solution containing an organic compound eluted at a methanol concentration of 84% or higher.

EXAMPLE 3

In example 3, glucose was produced using saliva from donkeys as the saliva of living matter. As comparison, glucose was also produced using saliva from cattle under the same conditions.

The cellulose raw material and the cellulolytic enzyme described in example 1 was used. In the present example, 500 µg of cellulase per 1 mL of the 50 mM buffer solution was suspended in the reaction mixture, and diluted ten-fold with the reaction mixture. Finally, a 50 µg/mL enzyme was used herein.

Details of the samples are as follows: sample a1 was obtained by adding 15 µL of the 50 µg/mL enzyme solution and 15 µL of the cattle saliva to 120 µL of the 10 µg/mL substrate suspension; sample a2 was obtained by adding only 15 µL of the cattle saliva to 120 µL of the 10 µg/mL substrate suspension, and adjusting the resultant to a total amount of 150 µL with the buffer solution; sample b1 was obtained by adding 15 μL of the 50 μg/mL enzyme solution and 15 μL of the donkey saliva to 120 μL of the 10 μg/mL substrate suspension; sample b2 was obtained by adding only 15 μL of the donkey saliva to 120 μL of the 10 μg/mL substrate suspension, and adjusting the resultant to a total amount of 150 μL with the buffer solution; and sample c was obtained by adjusting only 120 μL of the 10 μg/mL substrate suspension to a total amount of 150 μL with the buffer solution. Incubation for 24 hours at 50° C. was performed on each sample. The calculation results of the obtained reducing sugar are shown in FIG. 4.

Figure 4:
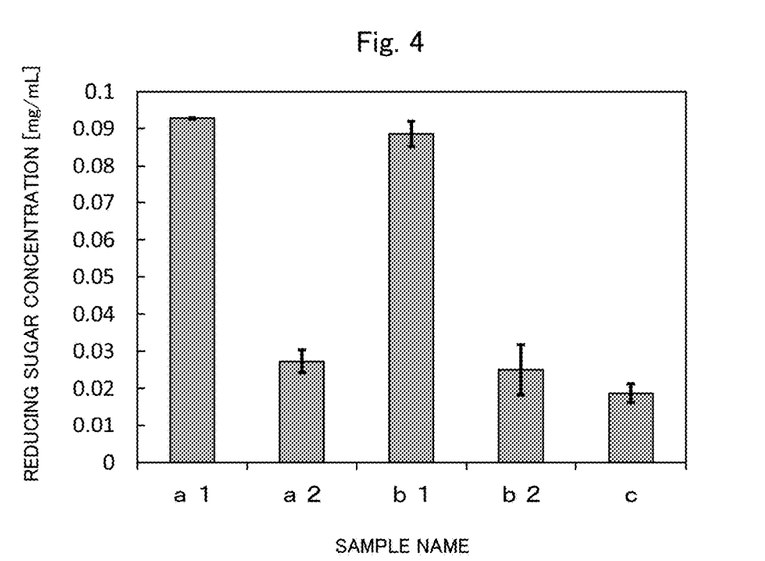
FIG. 4 is a graph of the glucose yield from each sample in example 3 of the glucose production method of the present invention.

In the present example, as shown in FIG. 4, 0.09 mg/mL of reducing sugar was detected from sample a1 in which 15 μL of the 50 μg/mL enzyme solution and 15 μL of the cattle saliva had been added and for which the glucose production method of the present invention was used; 0.03 mg/mL of reducing sugar was detected from sample a2 in which only 15 μL of the cattle saliva had been added; 0.09 mg/mL of reducing sugar was detected from sample b1 in which 15 μL of the 50 μg/mL enzyme solution and 15 μL of the donkey saliva had been added; 0.03 mg/mL of reducing sugar was detected from sample b2 in which only 15 μL of the donkey saliva had been added; and 0.02 mg/mL of reducing sugar was detected from sample c containing only the 10 μg/mL substrate suspension. The values indicated in FIG. 4 are the mean values of three samples, and the standard deviations thereof are indicated as error bars.

Based on the results, about three-times the amount of reducing sugar was detected from sample a1 and sample b1 for which the glucose production method of the present invention had been used, compared to that of sample a2 and sample b2 in which only the cellulase had been added to the cellulose raw material C. It is clear that enzymatic activity of the cellulase significantly improves as a result of cattle saliva, as well as donkey saliva, being added.

EXAMPLE 4

In example 4, to examine the relationship between the concentration of cattle saliva and the glucose yield, glucose was produced using cattle saliva at concentrations ranging from 0% to 10%, with undiluted cattle saliva being 100%.

The cellulose raw material and the cellulolytic enzyme described in example 1 was used. Undiluted cattle saliva was diluted with the buffer solution to 0.5%, 1%, 2%, 3%, 4%, 5%, 6%, 7%, 8%, 9%, and 10%, respectively, and used as the cattle saliva.

In the glucose production method in the present example, first, 20 μL of the 100 μg/mL enzyme solution and 20 μL of the cattle saliva were added to 160 μL of the 10 μg/mL substrate suspension serving as the cellulose raw material C. Incubation was then performed for 24 hours at 50° C. The results of calculation of reducing sugar concentrations using the Somogyi-Nelson method after incubation are indicated in FIG. 5.

Figure 5:
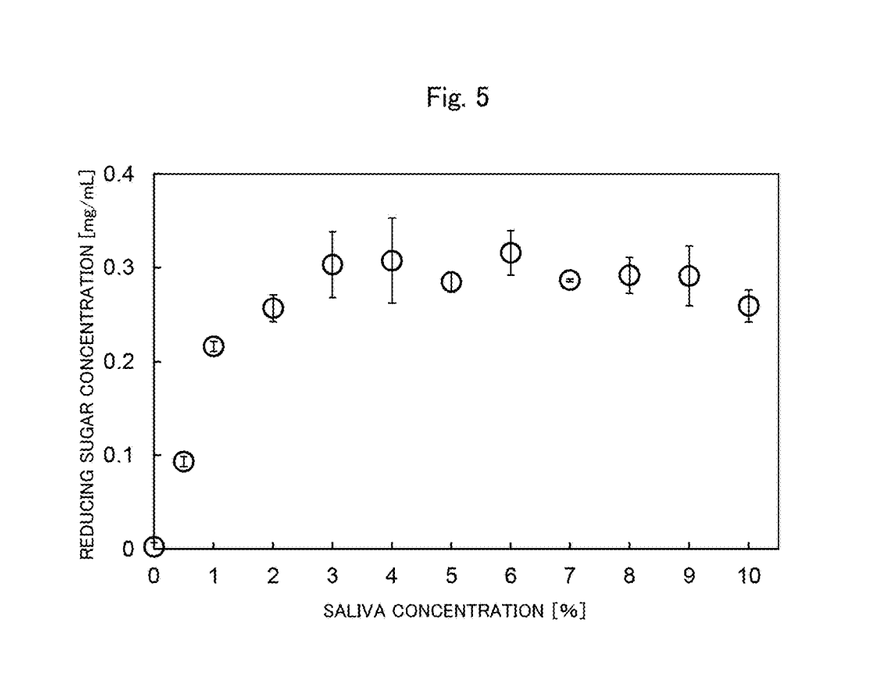
FIG. 5 is a graph of the glucose yield from each sample in example 4 of the glucose production method of the present invention.

In the present example, as shown in FIG. 5, glucose yield sharply increased up to the saliva concentration of 2%. Glucose yield was substantially equal from the saliva concentrations of 2% to 10%.

The results indicate that, as a result of the cattle saliva concentration being set to 2% or higher, more glucose can be collected from the same amount of cellulose raw material.

EXAMPLE 5

In example 5, to examine the relationship between incubation time and glucose yield, glucose was produced while changing the incubation time over a range from 0 to 72 hours.

The cellulose raw material, the cellulolytic enzyme, and the cattle saliva described in example 1 were used. As a sample for comparison, glucose was produced by adding only a cellulolytic enzyme to the cellulose raw material serving as a substrate.

Figure 6:
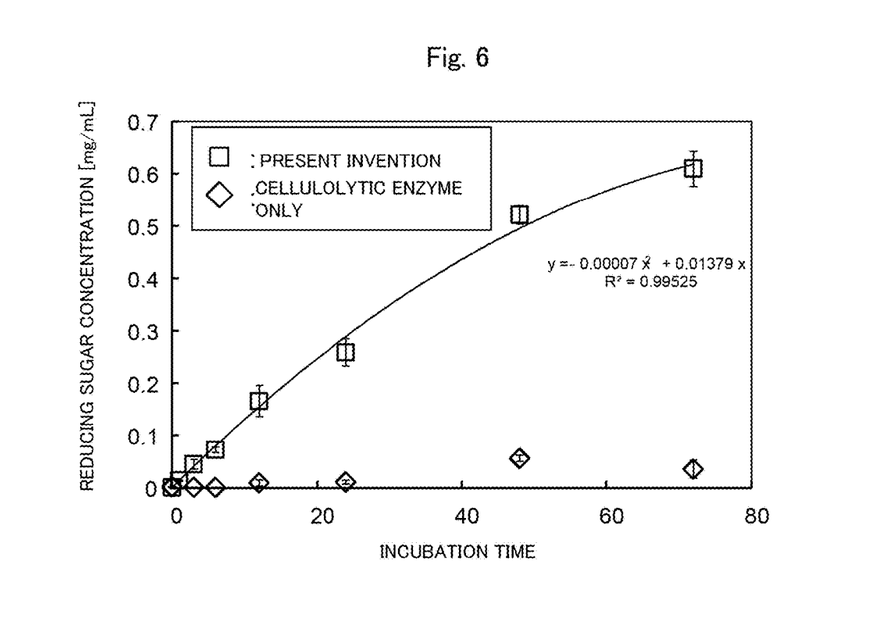
FIG. 6 is a graph of the glucose yield from each sample in example 5 of the glucose production method of the present invention.

In the glucose production method in the present example, first, 20 μL of the 100 μg/mL enzyme solution and 20 μL of the cattle saliva were added to 160 μL of the 10 μg/mL substrate suspension serving as the cellulose raw material C. Incubation was then performed for 0 hours, 3 hours, 6 hours, 12 hours, 24 hours, 48 hours, and 72 hours, respectively, at 50° C. The results of calculation of reducing sugar concentrations using the Somogyi-Nelson method after incubation are indicated in FIG. 6. In a similar manner, incubation was performed for 0 hours, 3 hours, 6 hours, 12 hours, 24 hours, 48 hours, and 72 hours, respectively, at 50° C. on the sample in which only the cellulolytic enzyme had been added to the cellulose raw material, and glucose was thereby produced.

In the present example, as shown in FIG. 6, in the samples using the glucose production method of the present invention indicated by square symbols, glucose yield increased as the incubation time increased. Meanwhile, in the samples in which only the cellulolytic enzyme was added, no dependency of the glucose yield on incubation time could be found. In particular, at the incubation time of 72 hours, the glucose yield of the sample for which the glucose production method of the present invention was used was about 30-fold compared to that of the sample in which only the cellulolytic enzyme had been added.

Based on the results, it is clear that, in the glucose production method of the present invention, the glucose production amount can be significantly increased as a result of cattle saliva being added, in addition to the cellulolytic enzyme, and the incubation time being increased.

EXAMPLE 6

In example 6, to examine the production amount of glucose when the glucose production method of the present invention is applied to a water-soluble cellulose raw material, glucose was produced using carboxymethyl cellulose (CMC; manufactured by Nacalai Tesque, Inc.).

The cellulolytic enzyme and the cattle saliva described in example 1 were used. As a sample for comparison, glucose was produced by adding only the cellulolytic enzyme to the cellulose raw material serving as a substrate.

Figure 7:
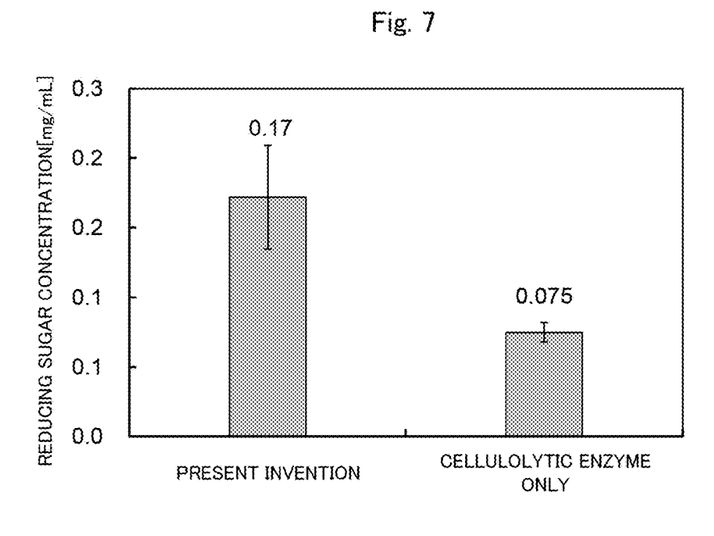
FIG. 7 is a graph of the glucose yield from each sample in example 6 of the glucose production method of the present invention.

In the glucose production method in the present example, first, 20 μL of the 100 μg/mL enzyme solution and 20 μL of the cattle saliva were added to 160 μL of the 10 μg/mL substrate suspension serving as the cellulose raw material C. Incubation was then performed for 30 minutes at 50° C. The results of calculation of reducing sugar concentrations using the Somogyi-Nelson method after incubation are indicated in FIG. 7. Glucose was also produced by a similar production method for the sample in which only the cellulolytic enzyme had been added to the cellulose raw material.

In the present example, as shown in FIG. 7, 0.17 mg/mL of glucose was obtained in the sample in which the cattle saliva had been added and for which the glucose production method of the present invention was applied. 0.0075 mg/mL of glucose was obtained in the sample in which only the cellulolytic enzyme had been added and cattle saliva had not been added.

Based on the results, it is clear that, regarding the water-soluble cellulose raw material as well, the glucose production amount can be increased through application of the glucose production method of the present invention.

EXAMPLE 7

In example 7, the specific working effect of cattle saliva will be described. As a preliminary experiment, the inventors of the present invention and the like examined the effects of cattle saliva on the crystalline form of the cellulose raw material. It was revealed that cattle saliva had no effect on the crystalline form of the cellulose raw material. Furthermore, through measurement of the static surface tension of cattle saliva, it became clear that cattle saliva acts as a surfactant.

In the present example, to clarify the target on which the cattle saliva acts, samples (i) to (iii) in which the cattle saliva had been added at differing timings were examined. First in sample (i), cattle saliva was added to the cellulose raw material, and incubation was performed for 1 hour at 50° C. Then, the cellulolytic enzyme was added, incubation was performed for 24 hours at 50° C., and glucose was thereby produced. In sample (ii), the cellulolytic enzyme was added to the cellulose raw material and incubation was performed for 1 hour at 50° C. Then, the cattle saliva was added, incubation was performed for 24 hours at 50° C., and glucose was thereby produced. In sample (iii), cattle saliva was added to the cellulolytic enzyme, and incubation was performed for 1 hour at 50° C. Then, the cellulose raw material was added, incubation was performed for 24 hours at 50° C., and glucose was thereby produced. In the present example, glucose was produced using 160 μL of the 10 μg/mL substrate suspension as the cellulose raw material C, 20 μL of the 100 μg/mL enzyme solution, and 20 μL of the cattle saliva. The results of calculation of reducing sugar concentrations using the Somogyi-Nelson method after incubation are indicated in FIG. 8.

Figure 8:
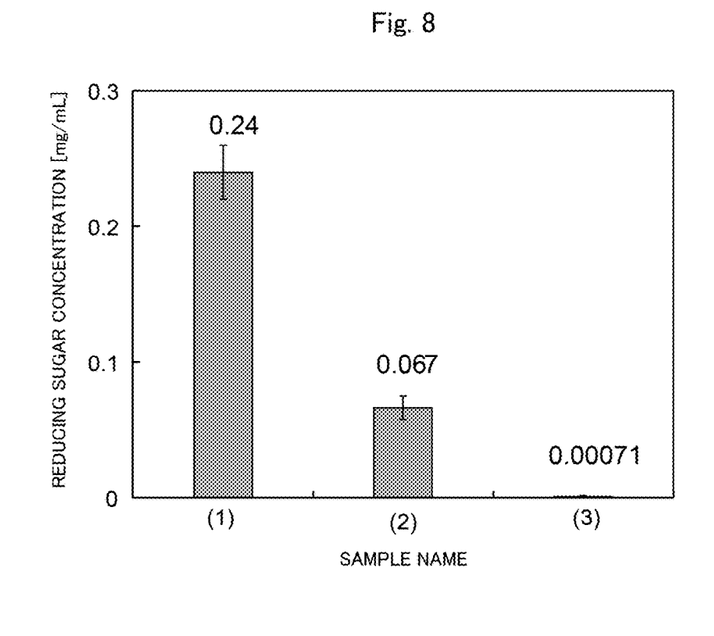
FIG. 8 is a graph of the glucose yield from each sample in example 7 of the glucose production method of the present invention.

In the present example, as shown in FIG. 8, 0.24 mg/mL of glucose was obtained from sample (i) in which the cellulolytic enzyme was added after cattle saliva had been added to the cellulose raw material. 0.067 mg/mL of glucose was obtained from sample (ii) in which the cattle saliva was added after the cellulolytic enzyme had been added to the cellulose raw material. 0.00071 mg/mL of glucose was obtained from sample (iii) in which the cellulose raw material was added after the cattle saliva had been added to the cellulolytic enzyme.

Based on the results, it is clear that, while the cattle saliva does not affect the crystalline form of the cellulose raw material, because the glucose yield from sample (i) was the highest, the cattle saliva attaches to the surface of the cellulose raw material and improves the working of the cellulolytic enzyme, added at the subsequent step, on the cellulose raw material. Therefore, in the glucose production method of the present invention, it is clear that the production method is preferably that in which, after the step at which the cattle saliva is added to the cellulose raw material and attached to the surface of the cellulose raw material, the step is performed in which the cellulolytic enzyme is added, the cellulose is decomposed, and glucose is produced.

EXAMPLE 8

In example 8, to examine the characteristics of the activating auxiliary agent derived from biological saliva in further detail, glucose was produced using activating auxiliary agents in which cattle saliva had been denatured and fractionated by molecular weight.

In the present example, first, to denature oxygen that is active in the cattle saliva and deactivate the oxygen, 15 mL of ethanol at a concentration of 99.5% was added to 5 mL of cattle saliva. High-speed centrifugation was then performed for 20 minutes at 15000 rpm at 4° C. Solvent removal was performed on the obtained supernatant liquid using an evaporator. To the resultant, 5 mL of ultra-pure water prepared using an ultra-pure water apparatus manufactured by Merck Millipore Corporation was added, and an ethanol denaturing activating auxiliary agent solution (sample A) was obtained.

In addition, to perform molecular-weight fractionation of the cattle saliva, 2 mL of sample A was subjected to high-speed centrifugation for 15 minutes at 3000 rmp at 4° C. using a centrifugal-type filter (UFC 910024; manufactured by Merck Millipore Corporation) that uses an ultrafilter membrane having a fractionation molecular-weight cut-off value of 100 K, and molecular-weight fractionation was thereby performed. An activating auxiliary agent solution (sample B) having a molecular weight of 100 K or lower was obtained.

In a similar manner, 2 mL of sample B was subjected to high-speed centrifugation for 15 minutes at 3000 rmp at 4° C. using a centrifugal-type filter (UFC 903008; manufactured by Merck Millipore Corporation) that uses an ultrafilter membrane having a fractionation molecular-weight cut-off value of 30 K, and molecular-weight fractionation was thereby performed. An activating auxiliary agent solution (sample C) having a molecular size of 30 K or lower was obtained. Furthermore, 2 mL of sample C was subjected to high-speed centrifugation for 15 minutes at 3000 rmp at 4° C. using a centrifugal-type filter (UFC 900308; manufactured by Merck Millipore Corporation) that uses an ultrafilter membrane having a fractionation molecular-weight cut-off value of 3 K, and molecular-weight fractionation was thereby performed. An activating auxiliary agent solution (sample D) having a molecular weight of 3 K or lower was obtained.

In the glucose production method of the present example, first, 20 μL of the 100 μg/mL enzyme solution serving as the cellulolytic enzyme and 20 μL of the ethanol denaturing activating auxiliary agent solution that is sample A were added to 160 μL of the 10 μg/mL substrate suspension serving as the cellulose raw material C. Incubation was then performed for 24 hours at 50° C. The reducing sugar concentration was calculated using the Somogyi-Nelson method after incubation. The cellulose raw material C and the cellulolytic enzyme described in example 1 were used.

Figure 9:
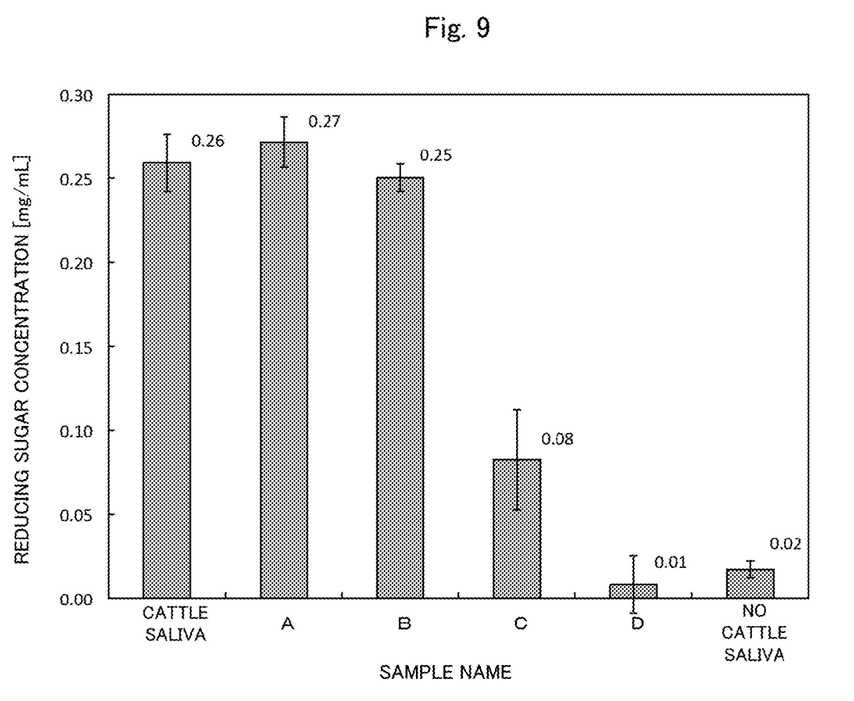
FIG. 9 is a graph of the glucose yield from each sample in example 8 of the glucose production method of the present invention.

In similar processes, the sample A was replaced with samples B to D. The obtained results are shown in FIG. 9. In FIG. 9, to example the results for samples A to D, the calculation result for reducing sugar concentration of glucose produced in a similar manner using unprocessed cattle saliva is indicated as "cattle saliva", and the calculation result for reducing sugar concentration of glucose produced without using cattle saliva is indicated as "no cattle saliva".

In the present example, as shown in FIG. 9, 0.26 mg/mL of reducing sugar was detected when unprocessed cattle saliva was used; 0.27 mg/mL of reducing sugar was detected when sample A serving as an ethanol denaturing activating auxiliary agent was used; 0.25 mg/mL of reducing sugar was detected when sample B serving as an activating auxiliary agent having a molecular weight of 100 K or lower was used; 0.08 mg/mL of reducing sugar was detected when sample C serving as an activating auxiliary agent having a molecular weight of 30 K or lower was used; 0.01 mg/mL of reducing sugar was detected when sample D serving as an activating auxiliary agent having a molecular weight of 3 K or lower was used; and 0.02 mg/mL of reducing sugar was detected when no cattle saliva was used. The values indicated in FIG. 9 are the mean values of three samples, and the standard deviations thereof are indicated as error bars.

Based on the results, it is clear that, because the value of the reducing sugar concentration when sample A serving as the ethanol denaturing activating auxiliary agent solution is used is a substantially similar to that when the unprocessed cattle saliva is used, the active enzyme that is contained in cattle saliva is not a causative substance that promotes the enzymatic activity of the cellulolytic enzyme. In addition, because the reducing sugar concentration when sample D serving as the activating auxiliary agent having a molecular weight of 3 K or lower is used is lower than that when no cattle saliva is used, it is clear that the organic polymers having a molecular weight of 3 K or lower that are contained in cattle saliva are also not causative substances that promote the enzymatic activity of the cellulolytic enzyme. From these results, it has been revealed that the activating auxiliary agent derived from cattle saliva is the organic polymers having a molecular weight of 3 K or higher, including denatured proteins.

EXAMPLE 9

In example 9, to identify the components in the activating auxiliary agent derived from biological saliva, glucose was produced using cattle saliva that had been fractionated by molecular size by gel filtration chromatography as the activating auxiliary agent solution.

In the present example, molecular-size fractionation was performed using a liquid chromatography apparatus (AKTAprime, manufactured by GE Healthcare) on 4 mL of cattle saliva. The chromatography conditions were as follows.

Sample: cattle saliva
Sample injection amount: 4 mL
Column: HiLoad 16/600 Superdex 200 prep grade (manufactured by GE Healthcare)
Eluent: 150 mM aqueous sodium chloride
Flow rate: 1 mL/min
Eluate fractionation: 5 mL×24 (Fraction No. 1 to 24)

The fractionated eluates will hereafter be referred to as Fraction No. 1 to 24, respectively.

Next, sodium dodecyl sulfate (SDS) polyacrylamide gel electrophoresis (12.5% gel) was performed on the obtained eluates of Fraction No. 1 to 24. The results obtained by proteins being silver-stained using Silver Stain KANTO III (manufactured by Kanto Chemical Co., Inc.) are shown in FIG. 10.

Figure 10:
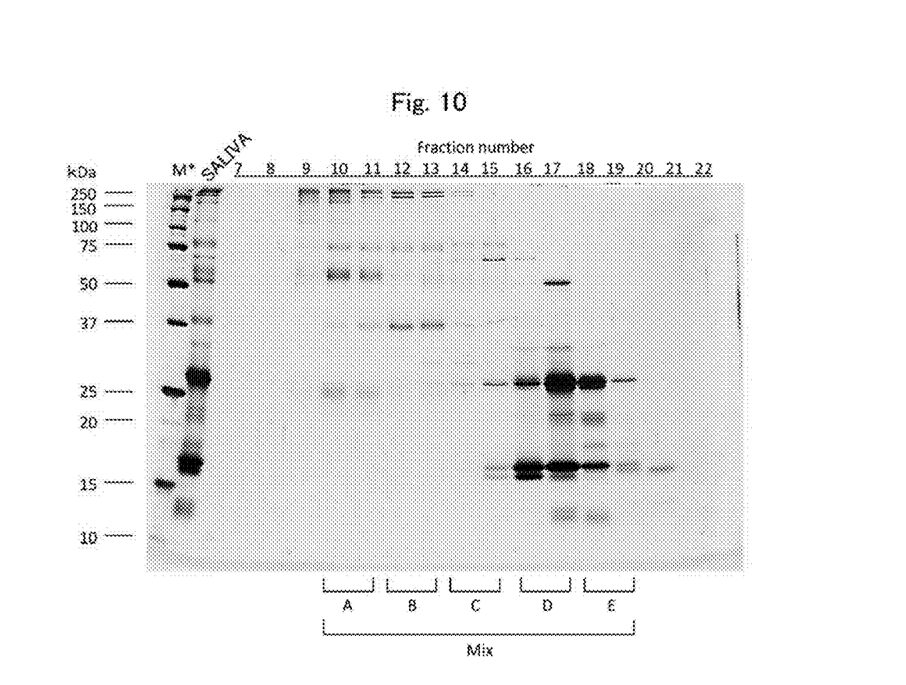
FIG. 10 is a silver stain image of each eluate that has undergone molecular size fractionation.

As shown in FIG. 10, of the eluates of Fraction No. 1 to 24, the presence of proteins was confirmed for the eluates of Fraction No. 9 to 20.

Samples A to E were then obtained by taking 2 mL of the eluates of No. 10 to No. 19, excluding the eluates of No. 9 and No. 20, two at a time and in sequence. A sample Mix was obtained by taking 0.4 mL each of the eluates No. 10 to No. 19 and combining. Each sample was concentrated using a centrifugal-type filter (UFC 900308; manufactured by Merck Millipore Corporation) that uses an ultrafilter membrane having a fractionation molecular-weight cut-off value of 3 K, and an eluate concentrate was obtained.

When the protein concentrations in the obtained eluate concentrates of samples A to E and Mix, as well as undiluted saliva, were measured, the protein concentration of each sample was as follows: 201.8 µg/mL in sample A; 174.5 µg/mL in sample B; 108.6 µg/mL in sample C; 795.7 µg/mL in sample D; 276.9 µg/mL in sample E; 366.2 µg/mL in sample Mix; and 1214.2 µg/mL in the undiluted saliva. An activity measurement test for cellulolytic enzyme was performed on eluate dilutions and a saliva solution obtained by adjusting the eluate concentrations of the samples and the undiluted saliva to a protein concentration of 40 µg/mL with ultra-pure water.

The activity promotion test for cellulolytic enzyme was conducted under the following conditions.

Substrate: 2 wt % substrate/100 mM sodium acetate buffer solution (pH=4.0)
Cellulolytic enzyme: 100 µg/mL of cellulase from Trichoderma Viride (manufactured by Sigma-Aldrich Corporation
Saliva solution: 40 µg/mL
Eluate dilution: samples A to E and sample Mix having a protein concentration of 40 µg/mL 80 µL of the substrate (final substrate concentration 0.8 wt %), 100 µL of the saliva solution or an eluate dilution (final protein concentration 20 µg/mL), and 20 µL of the cellulolytic enzyme (final enzyme concentration 10 µg/mL) were placed in a 1.5 mL plastic tube. Incubation was performed for 24 hours at 50° C. Centrifugal separation was performed for 1 minute at 15000 rpm. Quantification of the glucose concentration was performed on the obtained supernatant liquid using LabAssay Glucose kit (manufactured by WAKO Pure Chemical Industries, Ltd.). The obtained results are shown in FIG. 11.

Figure 11:
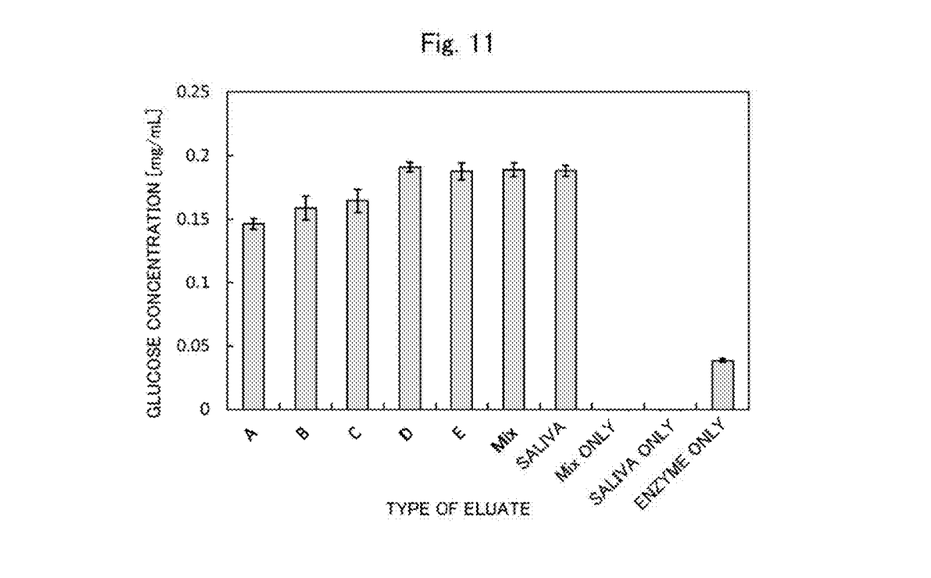
FIG. 11 is a graph of the glucose yield from each sample in example 9 of the glucose production method of the present invention.

As shown in FIG. 11, a higher glucose concentration was found when glucose was produced using the eluate dilutions of samples A to E and sample Mix, and the saliva solution, compared to when glucose was produced using only the enzyme. It has been confirmed that cellulolytic enzyme activity is promoted as a result of the eluate dilution or the saliva being added. As a result, it is clear that the activating auxiliary agent derived from biological saliva that promotes enzymatic activities of the cellulolytic enzyme is protein. In addition, because significant differences in glucose concentration were not found among the eluate dilutions, it is clear that the activity promoting effect can be obtained regardless of the type of protein, as long as the protein is contained in the biological saliva.

From the descriptions above, the glucose production method of the present invention relates to a method for producing glucose through enzymolysis of the cellulose raw material C. As a result of enzymolysis being performed by adding saliva from living matter or an activating auxiliary agent derived from biological saliva, in addition to the cellulolytic enzyme, glucose yield can be significantly improved. In addition, as a result, the produced glucose can be provided on the market at a low price.

The glucose production method of the present invention is not limited to the above-described embodiment. Various modifications are possible to an extent that the characteristics of the invention are not compromised. For example, enzymolysis of the cellulose may be performed using a mixture containing all of a cellulolytic enzyme, saliva from a ruminant animal, and an activating auxiliary agent derived from biological saliva. As a result of combining the saliva and the activating auxiliary agent derived from biological saliva, cellulolytic enzyme activity can be further improved.

The invention claimed is:
1. A method for producing glucose, comprising:
providing a cellulose raw material;
pulverizing the cellulose raw material to obtain a fine cellulose material;

enzymolytically decomposing the fine cellulose material using a mixture of a cellulolytic enzyme and either saliva obtained from a ruminant animal or an activating auxiliary agent isolated from saliva obtained from a ruminant animal, to obtain crude glucose material; and
purifying the crude glucose material to obtain a purified glucose material.

\* \* \* \* \*